United States Patent [19]
Lord

[11] Patent Number: 6,037,457
[45] Date of Patent: Mar. 14, 2000

[54] METHOD FOR RECOMBINANT FIBRINOGEN PRODUCTION

[75] Inventor: Susan T. Lord, Chapel Hill, N.C.

[73] Assignee: The University of North Carolina at Chapel Hill, Chapel Hill, N.C.

[21] Appl. No.: 08/792,108

[22] Filed: Jan. 31, 1997

[51] Int. Cl.[7] .............................. C07K 1/22; C07K 1/18; C07K 14/75; C12P 21/02
[52] U.S. Cl. ........................ 530/413; 435/69.6; 530/382; 530/412; 530/416; 530/420; 530/830
[58] Field of Search ..................................... 530/382, 380, 530/381, 412, 413, 418, 419, 416, 830, 829, 420; 435/69.1, 71.1, 70.1, 69.6, 70.3

[56] References Cited

U.S. PATENT DOCUMENTS

| | | | |
|---|---|---|---|
| 5,252,709 | 10/1993 | Busnouf et al. | 530/382 |
| 5,599,678 | 2/1997 | Kraus et al. | 435/7.9 |
| 5,723,579 | 3/1998 | Buettner et al. | 530/329 |

OTHER PUBLICATIONS

Lord et al. Biochemistry 35(7) 2342–2348, 1996.
Lord et al Blood Coagulation & Fibrinolysis 4 55–59, 1993.
Binnie et al Biochemistry 32(1) 107–113, 1993.
M.G. Bolyard and S.T. Lord, "High–level expression of a functional human fibrinogen gamma chain in *Escherichia coli*"; (1988) Gene, 66:183–192.
M.G. Bolyard and S.T. Lord, "Expression in *Escherichia coli* of the Human Fibrinogen Bβ Chain and Its Cleavage by Thrombin"; (1989) Blood, 75(5):1202–1206.
Binnie et al., "Characterization of Purified Recombinant Fibrinogen: Partial Phosphorylation of Fibrinopeptide A"; (1993) Biochemistry, 32:107–113.
Farrell et al., "Recombinant Human Fibrinogen and Sulfation of the γ' Chain"; (1991) Biochemistry, 30:9414–9420.
R. Hartwig and K.J. Danishefsky, "Studies on the Assembly and Secretion of Fibrinogen"; (1991) J. Biol. Chem., 266(10):6578–6585.
S.T. Lord, "Expression of a Cloned Human Fibrinogen cDNA in *Escherichia coli*: Synthesis of an A Alpha Polypeptide"; (1985) DNA, 4:33–38.
Roy et al., "Assembly and Secretion of Recombinant Human Fibrinogen"; (1991) J. Biol. Chem., 266(8):4758–4763.
D.H. Farrell and P. Thingarajan, "Binding of Recombinant Fibrinogen Mutants to Platelets"; (1994) J. Biol. Chem., 269(1):226–231.
Roy et al., "Secretion of Biologically Active Recombinant Fibrinogen by Yeast"; (1995) J. Biol. Chem., 270(40):23761–23767.

*Primary Examiner*—Nancy Degen
*Attorney, Agent, or Firm*—Myers Bigel Sibley & Sajovec, P.A.

[57] ABSTRACT

The present invention provides methods of producing recombinant fibrinogen in a long-term mammalian cell culture system. Disclosed is a method for the production of recombinant fibrinogen, comprising: growing mammalian cells that express recombinant fibrinogen in a serum-free medium for a time of at least one month at a level of at least 5 μg/ml; and then collecting portions of the conditioned medium at least twice during the culturing time of at least one month, with each portion containing at least 5 μg/ml of recombinant fibrinogen. Also disclosed is a method for the production of recombinant fibrinogen, comprising: growing mammalian cells that express recombinant fibrinogen in a serum-free medium at a level greater than 1 μg/ml; collecting at least a portion of the conditioned medium, and then purifying the fibrinogen from the medium by anion-exchange chromatography or affinity chromatography. In some embodiments of the invention, the medium is concentrated prior to the step of purifying the fibrinogen. In alternate embodiments, both the concentrating and purifying steps are carried out in the presence of at least one protease inhibitor.

44 Claims, 4 Drawing Sheets

PCR primers to incorporate mutations:

Bβ A68T - fibrinogen
                                     AvrII
                             CCCAGA[C▽CTAGG]GGTGTTGT ⟶ PCR2
PCR1 ⟵ AGAAGTG<u>TG</u>ACTGGGTCT[GGATC△C]CCACA Bβ P70S - fibrinogen
                                    BspEI
                              GCTGA[T▽CCGGA]C<u>T</u>CGGGGGTGT ⟶ PCR2
PCR1 ⟵ AGTGCGTACT[AGGCC△T]CGACCCC Bβ L72S - fibrinogen
                                    AvrII
                            CCCAGA[C▽CTAGG]GGTGTTGT ⟶ PCR2
PCR1 ⟵ CGACTG<u>AG</u>TCT[GGATC△C]CCACAA

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "oligonucleotide"

(xi) SEQUENCE DESCRIPTION: SEQ ID NO:1:

TTGAGATCTG GCCATACACT TGAGT    25

(2) INFORMATION FOR SEQ ID NO:2:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "oligonucleotide"

(xi) SEQUENCE DESCRIPTION: SEQ ID NO:2:

AACCTCTACA AATGTGGTAT GGCTG    25

(2) INFORMATION FOR SEQ ID NO:3:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "oligonucleotide"

(xi) SEQUENCE DESCRIPTION: SEQ ID NO:3:

ACACCCCTAG GTCTGGGTCA GTGTGAAGA    29

(2) INFORMATION FOR SEQ ID NO:4:

(i) SEQUENCE CHARACTERISTICS:

-continued

```
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:4:

CCCCAGCTCC GGATCAGCGT GA                                              22

(2) INFORMATION FOR SEQ ID NO:5:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:5:

AACACCCCTA GGTCTGAGTC AGC                                             23

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:6:

CCCAGACCTA GGGGTGTTGT                                                 20

(2) INFORMATION FOR SEQ ID NO:7:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:7:

GCTGATCCGG ACTCGGGGGT GT                                              22
```

METHOD FOR RECOMBINANT FIBRINOGEN PRODUCTION

This invention was made with Government support under Grant Number HL31048 and HL45100 from the National Institutes of Health. The Government has certain rights to this invention.

FIELD OF THE INVENTION

The present invention relates to methods of recombinant protein production, in particular to methods of producing recombinant fibrinogen.

BACKGROUND OF THE INVENTION

Fibrinogen is a soluble plasma protein consisting of two pairs of three protein chains designated Aα, Bβ, and γ to give a configuration of $(A\alpha B\beta\gamma)_2$ for the intact fibrinogen molecule. The Aα, Bβ, and γ chains interact by a series of 29 disulfide bonds among the six protein chains. Fibrinogen is converted to insoluble fibrin by the action of thrombin and Factor XIIIa. Thrombin cleaves four short fibrinopeptides from fibrinogen: two fibrinopeptide A (FpA) fragments and two fibrinopeptide B (FpB) fragments from the amino termini of the Aα and Bβ chains, respectively. The resulting six chain proteins are monomers, which assemble to form a fibrin matrix; this fibrin matrix is the principal component of blood clots.

Bacterial systems have been used to express the individual recombinant fibrinogen chains as monomers. Bolyard and Lord, Blood, 73, 1202 (1989); Bolyard and Lord, Gene 66, 183 (1988); Lord, DNA, 4, 33 (1985). A significant drawback of bacterial expression systems is that they cannot produce intact, biologically active fibrinogen molecules. Intact human fibrinogen has been expressed in yeast. Roy et al., J. Biol. Chem. 270, 23761 (1995).

Farrell et al., Biochemistry 30, 9414 (1991) disclose a method of producing recombinant human fibrinogen in BHK (baby hamster kidney) and HepG2 human liver cells. These investigators employed the BHK and HepG2 systems to study post-translational modification of fibrinogen variants. Farrell et al. also disclose a method of purifying recombinant fibrinogen from conditioned BHK and HepG2 culture media by immunoprecipitation with protein A-SEPHAROSE®. The immunopurified material was used for analytical purposes in clotting assays and chromatographic and electrophoretic analysis. Likewise, Roy et al., J. Biol. Chem. 266, 4758 (1991) purified recombinant human fibrinogen from COS-1 cells and Hartwig and Danishefsky, J. Biol. Chem. 266, 6578 (1991) purified recombinant human fibrinogen from COS-1, HepG2 and HepG3 cells by immunoprecipitation for analytical characterization.

Binnie et al., Biochemistry 32, 107 (1993), disclose a method of producing recombinant human fibrinogen in cultures of Chinese Hamster Ovary (CHO) cells using a two-step transfection procedure. First, CHO cells are cotransfected with expression vectors encoding the Aα and γ chains of human fibrinogen. Cell lines derived from clones expressing high levels of both the Aα and γ chains are then cotransfected with a Bβ chain expression vector to give cell lines expressing all three recombinant human fibrinogen chains. The recombinant Aα, Bβ, and γ chains assemble to form intact human fibrinogen. The recombinant human fibrinogen is purified from the conditioned culture medium by protamine SEPHAROSE® chromatography. One disadvantage of the method of Binnie et al. is that the recombinant fibrinogen is present at low concentrations in large volumes of conditioned culture medium. Both the yield and purity of the purified fibrinogen are adversely affected under these conditions.

Farrell et al., J. Biol. Chem. 269, 226 (1994), disclose a method of purifying recombinant human fibrinogen from cultures of BHK cells by two sequential rounds of affinity chromatography. First, the conditioned culture medium is passed through a protamine-agarose column. The fibrinogen in the eluate is further purified over a column bearing immobilized peptide corresponding to the carboxyl terminus of the fibrinogen γ chain. This method also results in large volumes of conditioned culture medium containing only low concentrations of fibrinogen; Farrell et al. state that the conditioned culture medium was applied to the protamine-agarose column at 30–40 ml/hour over a five-day period. Id. at page 227.

Accordingly, there remains a need in the art for improved methods of producing and purifying recombinant fibrinogen from long-term mammalian cell cultures.

SUMMARY OF THE INVENTION

As a first aspect, the present invention provides a method for the production of recombinant fibrinogen, comprising: growing mammalian cells that express recombinant fibrinogen in a serum-free medium in a container for a time of at least one month under conditions that cause the expression of fibrinogen in the medium at a level of at least 5 μg/ml; and then collecting portions of the medium at least twice during the time of at least one month, each of the portions containing at least 5 μg/ml of recombinant fibrinogen.

As a second aspect, the present invention provides a method for the production of recombinant fibrinogen, comprising: growing mammalian cells that express recombinant fibrinogen in a serum-free medium under conditions that cause the expression of fibrinogen in the medium at a level greater than 1 μg/ml; then collecting at least a portion of the medium containing greater than 1 μg/ml of recombinant fibrinogen; and then purifying the fibrinogen from the medium by anion-exchange chromatography or affinity chromatography with protamine-agarose or a monoclonal antibody.

As a third aspect, the present invention provides a method for the production of recombinant fibrinogen, comprising: growing mammalian cells that express recombinant fibrinogen in a serum-free medium under conditions that cause the expression of fibrinogen in the medium at a level greater than 1 μg/ml; then collecting at least a portion of the medium containing greater than 1 μg/ml of recombinant fibrinogen; and then concentrating the fibrinogen from the medium to form a concentrated medium; and then purifying the fibrinogen from the concentrated medium by anion-exchange chromatography or affinity chromatography.

As a fourth aspect, the present invention provides a method for the production of recombinant fibrinogen, comprising: growing mammalian cells that express recombinant fibrinogen in a serum-free medium under conditions that cause the expression of fibrinogen in the medium at a level greater than 1 μg/ml; then collecting at least a portion of the medium containing greater than 1 μg/ml of recombinant fibrinogen; and then concentrating the fibrinogen from the medium by precipitation with ammonium sulfate to form a concentrated medium; and then purifying the fibrinogen from the concentrated medium by anion-exchange chromatography or affinity chromatography with protamine-agarose or a monoclonal antibody; and wherein the concentrating and purifying steps are carried out in the presence of at least one protease inhibitor.

The foregoing and other aspects of the present invention are explained in the Detailed Description set forth below.

BRIEF DESCRIPTION OF THE DRAWINGS

FIG. 1A is a schematic representation of the DNA fragments assembled into the three altered plasmid expression vectors.

FIG. 1B shows the PCR primer sequences used to introduce the mutations into the Bβ chain cDNA. The novel codons for the variant residues are noted in underlined bold type. The new restriction sites are enclosed in brackets.

FIG. 2A shows the progress curves for fibrinopeptide release for normal recombinant fibrinogen.

FIG. 2B shows the progress curves for fibrinopeptide release for Bβ A68T fibrinogen.

FIG. 2C shows the progress curves for fibrinopeptide release for Bβ L72S fibrinogen.

FIG. 2D shows the progress curves for fibrinopeptide release for Bβ P70S fibrinogen.

DETAILED DESCRIPTION OF THE INVENTION

Figures 1A, 1B:
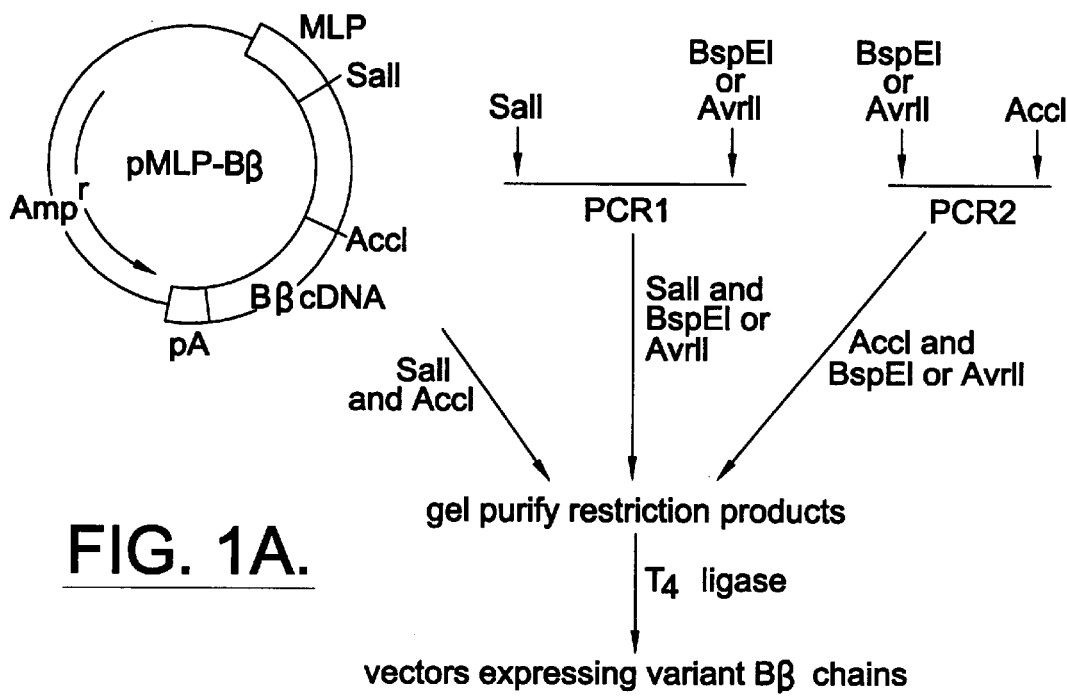
FIGS. 1A–B shows the construction of the altered Bβ-chain expression vectors.
Figure 2A:
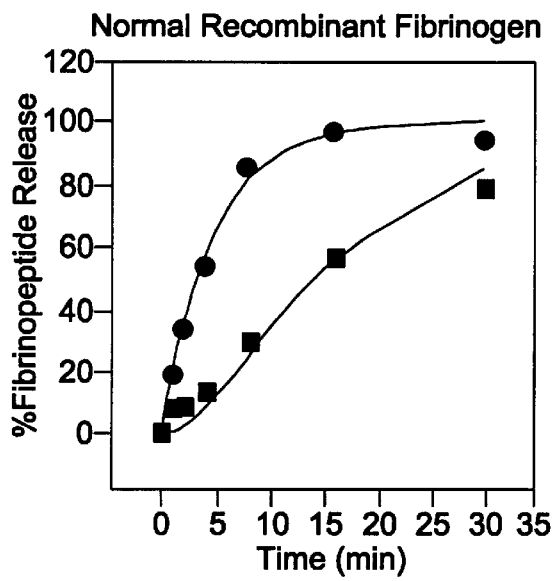
FIGS. 2A–2D presents progress curves for fibrinopeptide release from protamine-SEPHAROSE® purified recombinant fibrinogen. The thrombin-catalyzed release of FpA (●) and FpB (■) was monitored by HPLC. All reactions were run at ambient temperature in 50 mM Tris-HCl, pH=7.4, 0.15M NaCl; the fibrinogen concentration was 0.4 $\mu$M; for normal fibrinogen, Bβ P70S-fibrinogen and Bβ L72S-fibrinogen, α-thrombin was 0.043 U/ml; for Bβ A68T-fibrinogen, α-thrombin was 0.43 U/ml. The line through the data for FpA is from Equation 1; the line for FpB is from Equation 2.
Figure 2B:
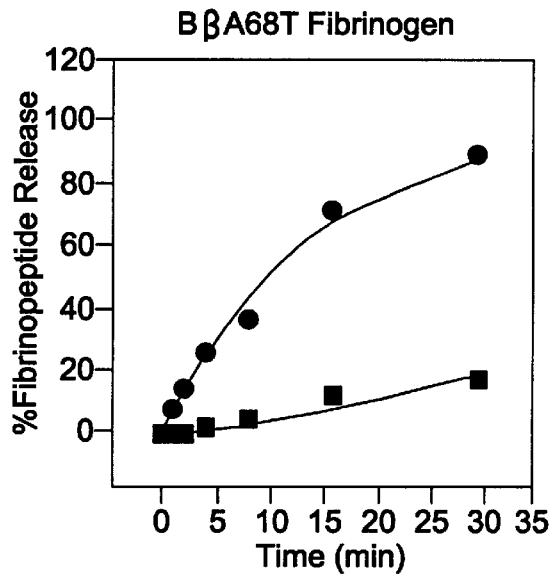
Figure 2C:
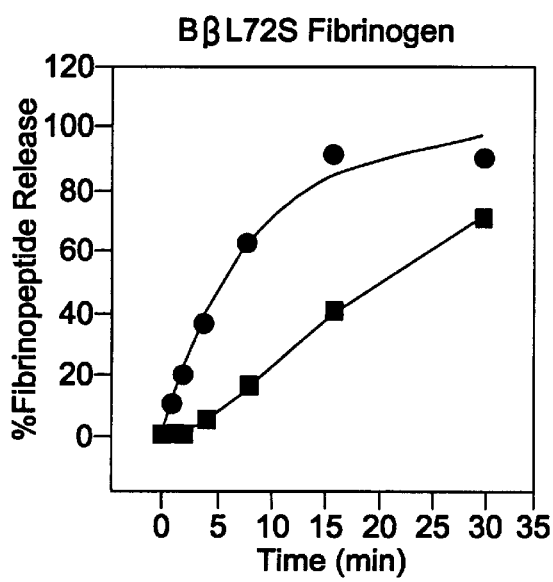
Figure 2D:
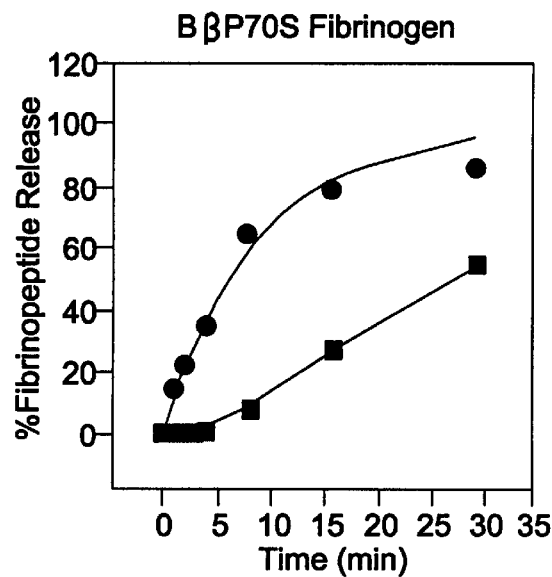

Nucleotides and amino acids are represented herein in the manner recommended by the IUPAC-IUB Biochemical Nomenclature Commission and in accordance with 37 CFR § 1.822 and established usage. In the description of the invention and the Examples hereinbelow, "bp" means base pair, "kDa" means kiloDalton "s" means second, "min" means minute, "h" means hour, "U" means unit, "IU" means International Unit, "$\mu$g" means microgram, "mg" means milligram, "$\mu$l" means microliter, "ml" means milliliter, "L" means liter, "mol" means mole, "nM" means nanomolar, "$\mu$M" means micromolar, "mM" means millimolar, "nm" means nanometer, "mm" means millimeter, and "kV" means kilovolt.

There is considerable interest in identifying a safe, efficient and cost-effective method of producing recombinant fibrinogen. Fibrinogen from natural sources has two primary disadvantages: contamination by impurities and pathogens. On the other hand, current methods of producing recombinant fibrinogen using transgenic animals are time-consuming, expensive, and still pose the problem of pathogen transmission. The present invention provides novel methods of producing recombinant fibrinogen using mammalian cell cultures that is efficient, cost-effective, and safe for veterinary or medical uses. Fibrinogen produced by the claimed methods, for example, finds use as a component of "fibrin glues."

The term "fibrinogen," as used herein, encompasses both native fibrinogens, including allelic variants and non-allelic variants (e.g., fibrinogen containing a γ' chain as described by Farrell et al., Biochemistry 30, 9414 (1991)), and mutant fibrinogens. Mutant fibrinogens, sometimes called "dysfibrinogens," can either be naturally-occurring or produced in the laboratory by any suitable method, such as site-directed mutagenesis. See Kunkel, Proc. Natl. Acad. Sci. USA 82, 488 (1985). Alternatively, mutations may be introduced by replacement of homologous restriction fragments in the cDNAs which encode the fibrinogen chains, in accordance with known procedures. Mutant fibrinogens are known to those skilled in the art. Exemplary mutant fibrinogens include, but are not limited to, human fibrinogen with an Ala to Thr substitution at the 68 position of the Bβ chain (fibrinogen Naples; Koopman et al., J. Clin. Invest. 90, 238 (1992)), and human fibrinogen in which amino acids 9–72 of the Bβ chain are missing (fibrinogen New York I; Liu et al., J. Biol. Chem. 260, 4390 (1985)). Other mutant fibrinogens are described in R. F. EBERT, INDEX OF VARIANT HUMAN FIBRINOGENS (CRC Press, 1994). See also, Shafer and Higgins, CRC Critical Reviews in Clinical Laboratory Sciences 26, 1, 6–7 (1988). Thus, mutant fibrinogens may contain point mutations, substitution mutations, deletion mutations, or insertion mutations.

The present invention provides a method of producing recombinant fibrinogen in mammalian cell cultures. In one embodiment of the invention, recombinant fibrinogen is produced by growing mammalian cells expressing recombinant fibrinogen in culture and then collecting portions of the conditioned medium containing the expressed recombinant fibrinogen therein. The mammalian cells are grown in a container in serum-free medium. Any suitable container can be used to carry out the claimed method. Illustrative containers include petri dishes, tissue culture dishes, tissue culture flasks, and roller bottles, with roller bottles being preferred. In a more preferred embodiment of the invention, the cells are grown on adherent microcarrier beads in roller bottles.

The mammalian cells expressing the recombinant fibrinogen are cultured for a period sufficient for accumulation of fibrinogen in the conditioned culture medium. The mammalian cells can be cultured for a period of two weeks, at least one month, two to three months, four months, six months or more. At least a portion of the culture medium conditioned by the mammalian cells is collected during the culturing period. In a preferred embodiment, portions of the conditioned culture medium are collected (and, preferably, replaced with fresh medium) at least twice during the culturing period. The collecting steps may be separated in time by two, three, four, five, six, or seven days or more. In general, media are collected more frequently with cell lines that produce high levels of fibrinogen and less frequently with cell lines that produce lower levels of fibrinogen. The collection steps may be carried out in any suitable manner that is convenient for a particular production schedule.

The cultured mammalian cells are cotransfected with expression vectors encoding the recombinant fibrinogen A$\alpha$, B$\beta$, and $\gamma$ chains (or allelic variations, non-allelic variants, and mutants thereof), and thereby express recombinant fibrinogen. By the phrases "express recombinant fibrinogen" or "expression of fibrinogen," it is meant that the recombinant genes encoding the fibrinogen A$\alpha$, B$\beta$, and $\gamma$ chains are transcribed into mRNAs, which are then translated into the A$\alpha$, B$\beta$, and $\gamma$ protein chains. Further, the protein monomers are post-translationally processed and assembled to form an intact fibrinogen molecule. Those skilled in the art will appreciate that some mutant fibrinogen chains will not associate correctly to give an intact fibrinogen molecule (e.g., with an (A$\alpha$B$\beta\gamma$)$_2$ configuration) and that some mutant fibrinogens may exhibit impaired function.

The production and use of cloned genes, recombinant DNA, vectors, transformed host cells, selectable markers, proteins, and protein fragments by genetic engineering are well-known to those skilled in the art. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. Applicants specifically intend that the disclosure of all United States patent references cited herein be incorporated herein by reference.

The mammalian cells are cultured under any suitable serum-free conditions that cause the expression of fibrinogen at a concentration of at least 1.0, 2.5, 5, 7.5, or 10 $\mu$g/ml of conditioned culture medium at each collection time. Thus, if the cells produce fibrinogen at a rate of 0.2 $\mu$g/ml of conditioned culture medium/day, the cells will have to be cultured for at least five days before each collection to achieve a fibrinogen concentration of at least 1 $\mu$g/ml of conditioned culture medium.

The cell culture conditions are tailored to the specific cell type. Any suitable serum-free medium known in the art is acceptable. Methods and media for culturing mammalian cells, in the presence or absence of serum, are well known in the art. See CELL CULTURE, in 58 Methods of Enzymology (William B. Jakoby & Ira H. Pastan eds., 1979); TISSUE CULTURE, (Kruse and Patterson eds., 1973). Fibrinogen cannot be expressed and collected in the presence of serum because proteases found therein will degrade the fibrinogen. Cells may be grown in the presence of serum for a period prior to the collection of fibrinogen in order to establish the cultures or let the cells recover from trypsinization. According to this embodiment, the cells are washed free of all serum prior to being switched to serum-free medium for the collection of fibrinogen. The formulation of the serum-free medium must include all essential nutrients and minerals. Insulin, transferrin, and selenium are common components of serum-free media. Insulin can be present at concentrations as low as $10^{-8}$, $10^{-9}$, $10^{-10}$ or $-10^{11}$M or lower, and as high as $10^{-8}$, $10^{-7}$ or $10^{-6}$M or higher. Transferrin can be present at concentrations as low as 5.0, 4.0, 3.0, 2.0, 1.0 or 0.5 $\mu$g/ml or lower, and as high as 5, 7.5, 10, 15 or 20 $\mu$g/ml or higher. Selenium can be added to the medium as a free element or in the form of a salt. Selenium can be present at concentrations as low as 5.0, 4.0, 3.0, 2.0, 1.0 or 0.5 $\mu$g/ml or lower, and as high as 5, 7.5, 10, 15 or 20 $\mu$g/ml or higher. In addition, serum-free media are frequently supplemented with steroid or protein hormones or peptide growth factors to promote cell growth and function. Bottenstein et al., Methods of Enzymology 58, 94 (1979), describe the use of hormones and growth factors as components of serum-free media. Cells are generally cultured at approximately a physiological temperature of 37° C. Typically, roller bottle cultures are not maintained under a controlled atmosphere, whereas cells cultured in an incubator are kept under a controlled atmosphere, such as 95% air/5% $CO_2$ or nitrogen and a relative humidity near saturation.

Illustrative conditions under which mammalian cells can be cultured to express fibrinogen are as follows: cells are grown in roller bottles with adherent microcarrier beads in a total of 200 ml of serum-free medium (Dulbecco's Modified Eagle's Medium/F12 medium containing 10 IU penicillin/ml, 10 mg streptomycin/ml, 10 U aprotinin/ml, and 10 $\mu$g/ml each of insulin, sodium selenite, and transferrin) at 37° C. for three weeks prior to commencing the collection of conditioned culture medium every four to seven days.

Mammalian cells used to express recombinant fibrinogen according to the present invention can be from any species, including mouse, hamster, rat, dog, pig, monkey, or human. Cells can be taken from fetal, neonatal, growing, or adult mammals. Mammalian cells used to produce the recombinant fibrinogen can be derived from any tissue or cell type, but preferably, the mammalian cells chosen have no or very low endogenous production of fibrinogen. Exemplary cell types include ovarian cells, kidney cells, and fibroblasts. Cultured cells can be primary cultures, serially-passaged cultures, and cultures of immortalized or transformed cell lines. In a preferred embodiment of the invention Chinese Hamster Ovary (CHO) cells are used to produce recombinant fibrinogen.

In one embodiment of the invention, the step of collecting the conditioned culture medium is followed by the step of purifying the recombinant fibrinogen secreted therein. The recombinant fibrinogen in the collected medium can be purified by any method known in the art, such as selective precipitation, affinity chromatography, dialysis, immunoprecipitation, ion-exchange chromatography, size-exclusion chromatography, hydrophobic interaction chromatography, or reversed-phase chromatography. See, Guide to Protein Purification, in METHODS OF ENZYMOLOGY v. 182 (Murray P. Deutscher ed., 1990), 2 REMINGTON: THE SCIENCE AND PRACTICE OF PHARMACY 534–58 (Alfonso R. Gennaro ed., 19th ed. 1995). Chromatography can be carried out using conventional columns or by HPLC (high performance liquid chromatography) or FPLC (fast protein liquid chromatography).

In one preferred embodiment of the invention, the recombinant fibrinogen is purified by anion-exchange chromatography. Methods of purifying proteins using anion-exchange chromatography are well known to those skilled in the art See, e.g., Edward R. Rossomando, Ion-Exchange Chromatography, in GUIDE TO PROTEIN PURIFICATION, METHODS OF ENZYMOLOGY 182, 309–16 (Murray P. Deutscher ed., 1990). In an alternate preferred embodiment of the invention, the fibrinogen is purified by affinity chromatography over a protamine-agarose column, such as a protamine-SEPHAROSE® (Pharmacia-LKB) column. Methods of purifying fibrinogen using protamine-agarose columns are known to those skilled in the art. See, e.g., Dempfle and Heene, Thromb. Res. 46, 19 (1987). Alternatively, fibrinogen can be purified by affinity chromatography using peptides with high affinity for fibrinogen. See, e.g., Farrell et al., J. Biol. Chem. 269, 226 (1994).

In another alternate preferred embodiment, the recombinant fibrinogen is purified by immunoaffinity chromatography using polyclonal or monoclonal antibodies raised against the intact fibrinogen molecule or one of the fibrinogen chains. Methods of producing and using polyclonal and monoclonal antibodies are well known in the art. See, e.g., ED HARLOW & DAVID LANE, ANTIBODIES: A LABORATORY MANUAL (1988); Norman A. Staines, Monoclonal Antibodies, in BIOCHEMICAL RESEARCH TECHNIQUES: A PRACTICAL INTRODUCTION (JOHN M. WRIGGLESWORTH ED., 1983). Likewise, methods of performing affinity chromatography using polyclonal and monoclonal antibodies are also well known in the art. See, e.g., ED HARLOW & DAVID LANE, ANTIBODIES: A LABORATORY MANUAL (1988); Steven Ostrove, Affinity Chromatography. General Methods, in GUIDE TO PROTEIN PURIFICATION, METHODS OF ENZYMOLOGY 182, 357–71 (Murray P. Deutscher ed., 1990).

The term "antibody" as used herein refers to all types of immunoglobulins, including IgG, IgM, IgA, IgD, and IgE. The term "immunoglobulin" includes the subtypes thereof, such as $IgG_1$, $IgG_2$, $IgG_3$, $IgG_4$, etc. Of these, IgM and IgG are preferred, and IgG is particularly preferred. The antibodies may be of any species of origin, including for example, mouse, rat, rabbit, horse, or human, or (in the case of monoclonal antibodies) may be chimeric antibodies. See, e.g., Walker et al., Molec. Immunol. 26, 403–11 (1989).

Monoclonal antibodies may be recombinant monoclonal antibodies produced according to the methods disclosed in U.S. Pat. No. 4,474,893 to Reading or U.S. Pat. No. 4,816,567 to Cabilly et al. The antibodies may also be chemically constructed by specific antibodies made according to the method disclosed in Segel et al., U.S. Pat. No. 4,676,980.

Monoclonal antibodies may be chimeric antibodies produced in accordance with known techniques. The monoclonal antibodies may be complementarity determining region-grafted antibodies (CDR-grafted antibodies) produced in accordance with known techniques.

Antibodies may be raised against the Aα, Bβ, or γ chains, or the intact fibrinogen molecule (including allelic variants, non-allelic variants, or mutants of the individual fibrinogen chains or the intact fibrinogen molecule). Alternately, antibodies may be raised against fragments of the individual fibrinogen chains or the fibrinogen molecule (including allelic variants, non-allelic variants, or mutants of the individual fibrinogen chains or the intact fibrinogen molecule). Monoclonal antibodies directed against fibrinogen are known in the art. Illustrative monoclonal antibodies include Mab-Y18, which recognizes the amino terminus of the Aα chain (see Lord and Fowlkes, Blood 73, 166 (1989)), the monoclonal antibody 4A5, which is specific for the carboxyl terminal residues of the γ-chain (Blumenstein et al., Biochemistry 31, 10692 (1992)), anti β, which is a monoclonal antibody that specifically recognizes the Bβ chain (Valenzuela et al., Amer. J. Pathol. 141, 861 (1992)), and the IF-1 monoclonal antibody, which was raised against the D fragment generated by elastase cleavage of the intact fibrinogen molecule (Takebe et al., Thromb. and Haemost. 73, 662 (1995)).

Previous attempts to purify recombinant fibrinogen from mammalian cell cultures have been hampered by the low fibrinogen concentrations found therein. In a further preferred embodiment of the invention, the recombinant fibrinogen in the collected medium as described hereinabove is concentrated prior to the step of purification as described hereinabove. Methods of concentrating protein solutions are well-known in the art and include lyophilization, dialysis and precipitation. More preferably, the recombinant fibrinogen in the collected medium is concentrated by precipitation with an ammonium sulfate solution. The concentration of ammonium sulfate is selected so as to precipitate the recombinant fibrinogen with a minimum of contaminants. The appropriate concentration of ammonium sulfate will vary inversely according to the concentration of the recombinant fibrinogen in the conditioned culture medium; the concentration of ammonium sulfate will increase as the concentration of recombinant fibrinogen in the conditioned culture medium decreases. Typically, ammonium sulfate solutions used to carry out the present invention will be 20%, 30%, 40%, or 50% saturated or higher.

In a further preferred embodiment of the present invention, both the concentration step and the purifying step, as described hereinabove, are carried out in the presence of one or more protease inhibitors. Typically, and more preferably, a "cocktail" of two or more, three or more, four or more, or even five or more protease inhibitors will be used during the concentration and purification steps. Illustrative protease inhibitors include, but are not limited to, soybean trypsin inhibitor, aprotinin, pepstatin, benzamide, benzamidine, sodium p-hydroxymercuribenzoate (PHMB), iodoacetate, N-ethylmaleimide, diazoacetylnorleucine methyl ester (DAN), leupeptin, ε-aminocaproic acid (ε-ACA), antipain, ethylenediaminetetraacetic acid (EDTA), ethylene glycol bis(β-aminoethyl ether) N,N,N',N'-tetraacetic acid (EGTA), and phenylmethylsufonyl fluoride (PMSF).

The following examples are provided to illustrate the present invention and should not be construed as limiting thereof.

EXAMPLE 1

Materials

All chemicals were reagent grade and, unless specified, were purchased from Sigma. The plasmid vectors, CHO cells, culture media, and immunologic reagents have been previously described. Binnie et al., Biochemistry 32, 107 (1993). Human fibrinogen, plasminogen free, was from Calbiochem. Human α-thrombin was a generous gift from Dr. Frank Church, Department of Pathology, University of North Carolina at Chapel Hill. Monoclonal antibody IF-1 was a generous gift from Dr. Michio Matsudo, Institute of Hematology, Jichi Medical School, Japan. Factor XIII (FXIII) was a generous gift from Dr. Kevin Siebenlist, Sinai-Samaritan Medical Center, Milwaukee, Wis.

EXAMPLE 2

Construction of Variant Expression Vectors

Three mutant fibrinogens were created to study thrombin-fibrinogen interactions as follows: A68T contains an Ala to Thr substitution at the 68 position of the Bβ chain, P70S contains a Pro to Ser substitution at the 70 position of the Bβ chain, and L72S contains a Leu to Ser substitution at the 72 position of the Bβ chain. The strategy for polymerase chain reaction (PCR)-directed mutagenesis of the Bβ chain cDNA is outlined in FIG. 1. Three altered cDNAs were constructed encoding the three mutant fibrinogen Bβ chains: each from two PCR products: PCR1, a 500 bp product beginning at the unique SalI site of the vector polylinker and ending with the codons surrounding the mutation, and PCR2, a 300 bp product beginning with the codons surrounding the mutation and ending at the AccI site in the codons for residues Val238 and Tyr239. The forward primer for all PCR1 products was 5'-TTGAGATCTGGCCATACACTTGAGT-3' (SEQ ID NO:1), which is the sequence just upstream from the SalI site. The reverse primer for all PCR2 products was 5'-AACCTCTACAAATGTGGTATGGCTG-3' (SEQ ID NO:2), which is the reverse sequence just downstream from the AccI site. The reverse primers for PCR1 were as follows: for A68T, 5'-ACACCCCTAGGTCTGGGTCAGTGTGAAGA-3' (SEQ ID NO:3), for P70S, 5'-CCCCAGCTCCGGATCAGCGTGA-3' (SEQ ID NO:4), and for L72S, 5'-AACACCCCTAGGTCTGAGTCAGC-3' (SEQ ID NO:5). The forward primer for PCR2 to incorporate both A68T and L72S was 5'-CCCAGACCTAGGGGTGTTGT-3' (SEQ ID NO:6). The forward primer for PCR2 to incorporate P70S was 5'-GCTGATCCGGACTCGGGGGTGT-3' (SEQ ID NO:7). The primers, which introduced the altered codons, also introduced restriction sites that were used to link the two PCR products without changing the encoded sequence or the reading frame of the altered cDNAs. For the A68T and L72S changes, an AvrII site was introduced; for the P70S change, a BspEI site was introduced. The expression plasmid, pMLP-Bβ, served as the template for the PCR reactions that used taq polymerase from Promega and reaction conditions recommended by the manufacturer. The reactions were cycled for 45 s at 95° C., 45 s at 55° C., and 30 s at 72° C. for 30 cycles. The PCR products were precipitated with ethanol, and the precipitates were dissolved in water and digested with the appropriate restriction enzymes. The digested bands were purified from agarose gels by electroelution and cloned into the parent vector, which was digested first with SalI and then with AccI, and purified by electroelution from an agarose gel. Cloning procedures were as described by Lord et al. J. Biol. Chem. 265, 838 (1990). Ligation products were transfected by electroporation into competent DH5α-F' cells. Colonies were screened by restriction digest analyses, and the Bβ cDNAs were sequenced using SEQUENASE® V2.0 as described by the manufacturer (US Biochemicals). No inadvertent changes arose during the mutagenesis procedures.

EXAMPLE 3

Recombinant Protein Expression

CHO cells expressing the normal Aα and γ-chains of human fibrinogen were prepared as previously described by Binnie et al., Biochemistry 32, 107 (1993), but using a new vector, pMLP-γ, to express normal fibrinogen γ-chain. The new vector was shown by DNA sequence analysis to contain the complete, normal γ-chain cDNA. The expressed γ-chain product reacts with the monoclonal antibody 4A5, which is specific for the carboxyl terminal residues of γ-chain in immunoblot analysis. Blumenstein et al., Biochemistry 31, 10692 (1992). Antibody 4A5 was kindly provided by Gary Matsueda, Bristol-Meyers Squibb Pharmaceutical Research Institute, Princeton, N.J. One G418 resistant cell line expressing Aα- and γ-chains was used for all the Bβ transfections. The normal Bβ expression vector, pMLP-Bβ, or one of the variant Bβ expression vectors described below was cotransfected with pMSVhis, and histidinol resistant cells were selected as previously described. Binnie et al., Biochemistry 32, 107 (1993). Cell lysates and culture media were analyzed by immunoblotting and ELISA, respectively. CHO lines producing useful concentrations were subcloned from single cells and grown in roller bottles for preparation of recombinant fibrinogens. Binnie et al., Biochemistry 32, 107 (1993).

EXAMPLE 4

Purification and Characterization of Recombinant Fibrinogen

CHO cells producing recombinant fibrinogens were maintained in roller bottles with adherent microcarrier beads in a total of 200 ml of serum-free medium: Dulbecco's Modified Eagle's Medium/F12 medium containing 10 IU penicillin/ml, 10 mg of streptomycin/ml, 10 U aprotinin/ml, and 10 μg/ml each of insulin, sodium selenite, and transferrin (Boehringer Mannheim). Starting 3 weeks after shifting to serum-free conditions, medium was harvested every 4–7 days by removing 100 ml from the culture and replacing it with 100 ml of fresh medium. Usually five or more roller bottles were grown from the same cell line. Harvested media were pooled, PMSF was added to 0.15 mM, and the fibrinogen concentration was determined by ELISA. Pooled media were stored at −80° C.

Prior to purification, the media were thawed in a 37° C. water bath just until the last solid disappeared. Thereafter, all manipulations were either on ice or at 0–4° C. Fibrinogen was precipitated from the media by addition of 40% saturated ammonium sulfate, as follows. In a 2 L flask, 1200 ml of medium was mixed with 30 ml of 40×buffer (50 mM Tris-HCl, pH=7.6, 100 mM NaCl, 200 mM ε-ACA, 80 mM EDTA, 400 U aprotinin/ml, 40 μM pepstatin, 40 μM leupeptin, and 200 mM benzamidine). With gentle, continuous stirring, 820 ml of saturated ammonium sulfate was added slowly by dripping through Whatman 3 mm paper. The suspension was left overnight without stirring, and the precipitate was collected in 250 ml bottles by centrifugation at 16,000 g for 30 min. After each spin, the supernatant was removed, fresh ammonium sulfate sample was added to the existing pellet, and centrifugation was repeated. Thus, the precipitate from each 2.05 L sample was collected in two bottles. The pellets were dissolved in 0.04 times the original medium volume of buffer A1: 50 mM Tris-HCl, pH=7.3, 150 mM NaCl, 5 mM ε-ACA, 2 mM EDTA, 10 U aprotinin/ml, 1 μM pepstatin, 1 μM leupeptin, 100 μM PMSF, and 5 mM benzamidine. The pellets were left on ice for several hours to dissolve, and centrifuged for 30 min at 16,000 g to remove undissolved material. The supernatant was applied to a protamine-SEPHAROSE® column, prepared as previously described (Dempfle & Heene, Thromb. Res. 46, 19 (1987)), and equilibrated with buffer A1. On the basis of the concentration measured by ELISA analysis of the media, 1 ml of resin was used for each 2 mg of fibrinogen. The column was washed, and fibrinogen eluted at pH=4.5 and was neutralized and dialyzed as previously described (Binnie et al., Biochemistry 32, 107 (1993)), with the addition that every buffer, aside from the pH=4.5 elution buffer contained the protease inhibitors: 5 mM ε-ACA, 2 mM EDTA, 10 U aprotinin/ml, 1 μM pepstatin, 1 μM leupeptin, 100 μM PMSF, and 5 mM benzamidine. The pH=4.5 elution buffer contained all the inhibitors except benzamidine, as this inhibitor obscured monitoring of protein elution by absorption at 280 nm. Inhibitors were added to buffers just prior to their use in each step. Purified fibrinogen was stored in the presence of inhibitors at −80° C. Aliquots of purified fibrinogen were monitored by SDS-PAGE and immunoblot analysis as described by Binnie et al. (Biochemistry 32, 107 (1993)).

EXAMPLE 5

Thrombin-Catalyzed Release of Fibrinopeptides

The thrombin-catalyzed release of FpA and FpB was measured by HPLC essentially as described by Ng et al., Methods Enzymol. 222, 341 (1993), but using the HPLC buffers described in Haverkate et al., Thromb. Haemostasis 55, 131 (1986). Prior to thrombin analysis, recombinant fibrinogens were dialyzed (MWCO =12,000–14,000) at 0–4° C. for 20 h against three changes of Tris-buffered saline (TBS) (50 mM Tris-HCl, pH=7.4, 150 mM NaCl) to remove protease inhibitors. The concentration of fibrinogen was determined by measuring the $\Delta A_{280-320}$ and assuming 10 mg of fibrinogen/ml gives a result of 15.1. Mihalyi, Biochemistry 7, 208 (1968). Aliquots of approximately 2 ml with $\Delta A=0.2$ were prepared in polypropylene tubes and equilibrated to ambient temperature. Human $\alpha$-thrombin, the generous gift of Dr. Frank Church, was diluted on ice in TBS in a polypropylene tube to a concentration of 4.3 U/ml. At time 0 min, thrombin was added to the fibrinogen sample to a final concentration of either 0.43 U/ml or 0.043 U/ml, as indicated in the results. The samples were mixed by gentle vortexing, and aliquots of 260 $\mu$l were dispensed as rapidly as feasible into seven 1.5 ml microfuge tubes. At the indicated times, reactions were terminated by incubating the aliquoted samples at 97–100° C. for>8 min. To prepare an infinite time point, 1 $\mu$l of thrombin at 4300 U/ml was added to the last aliquot and incubated at room temperature for approximately 25 min and heated at 97–100° C. for 5 min. After being heated, the tubes were centrifuged at 13,000 g for 15 min at 4° C., and the supernatants transferred to fresh tubes and stored at –20° C. prior to HPLC analysis.

EXAMPLE 6

Data Analysis

The concentrations of fibrinopeptides were determined by measuring the areas under the peaks on the HPLC chromatograms using the program provided by Isco (Chemresearch Chromatographic Data Management, Isco, Inc., Lincoln, Neb.), and comparing to areas from standard concentrations of fibrinopeptides. The peak areas for the infinite time points were consistent with the release of 2 mol of fibrinopeptide per mole of fibrinogen. The HPLC detector monitored absorbance at 205 nm, where the molar absorptivities for FpA and FpB are slightly different (Ng et al., Methods Enzymol. 222, 341 (1993)), we did not incorporate this difference into our analysis. HPLC chromatograms were also run for "zero" time points by mixing fibrinogen aliquots heated to 97–100° C. with thrombin also heated to 97–100° C., and these samples routinely did not have peaks eluting at the times for the fibrinopeptides. The data were plotted as progress curves. Using the program Enzfitter (Elsevier-Biosoft, Cambridge, U.K.), we initially fitted the FpA data to a first-order rate equation using the areas of the six time points plus a point of 0 min and 0 area plus the area of the infinite time point set arbitrarily at 300 min. From this fit we determined a "limit" area that was used as the area for maximal release of either fibrinopeptide. Each area was divided by this limit area, and plotted as the percent of fibrinopeptide release, using the software Sigma Plot (Jandel Scientific Software, San Rafael, Calif.). The FpA data were fitted to the standard equation that describes two sequential steps, each of which is a simple, first-order reaction. The basis for using these equations is summarized in Ng et al., Methods Enzymol. 222, 341 (1993). The Enzfitter program fitted the data by a nonlinear least-squares analysis and determined the standard error.

EXAMPLE 7

Synthesis and Characterization of Recombinant Fibrinogens

The altered vectors were transfected into the CHO line that expresses normal A$\alpha$ and $\gamma$-chains, as described in Example 3. The three transfections were performed together, and clones resistant to G418 and histidinol were concurrently picked, expanded, and assayed for fibrinogen. We found that 19 of 22 colonies from the A68T transfection, 25 of 29 colonies from the P70S transfection, and 14 of 15 colonies from the L72S transfection synthesized significant levels of fibrinogen. Thus, in all three transfections more than 86% of the colonies were fibrinogen positive. This is in marked contrast to the transfection that produced the CHO cell line that expresses normal A$\alpha$- and $\gamma$-chains. Here only 18% of the clones (four of 22 colonies) expressed both A$\alpha$- and $\gamma$-chains. The consistently high percent of positive clones, which expressed fibrinogens with abnormalities in a single chain, substantiated our choice of a two-step strategy.

Fibrinogen expression varied among these four CHO lines. Fibrinogen concentration in pooled samples for normal fibrinogen varied from 3 to 15 $\mu$g/ml; for A68T, from 1 to 6 $\mu$g/ml; for P70S, from 4 to 13 $\mu$g/ml; and for L72S, from 2 to 15 $\mu$g/ml. The fibrinogen concentration fluctuated in an apparently random manner, but frequently the highest synthesis was 20–40 days after the initial collection. Cultures were maintained and medium harvested until fibrinogen concentrations clearly decreased, which varied from 35 to 60 days.

Fibrinogen was purified as described in Example 4, incorporating two significant changes into the previously described procedure. Binnie et al., Biochemistry 32, 107 (1993). First, the fibrinogen was concentrated from the media by precipitation with 40% saturated ammonium sulfate. The precipitate was collected, dissolved in buffer, and applied to protamine-SEPHAROSE®. Second, every step of the purification was carried out in the presence of a cocktail of protease inhibitors. As previously reported (Binnie et al., Biochemistry 32, 107 (1993)), fibrinogen was eluted from protamine-SEPHAROSE® at pH=4.5, neutralized, dialyzed, and stored at –80° C. in the presence of protease inhibitors. Analysis of the purified fibrinogens by SDS-PAGE indicated that the proteins are reasonably pure and the individual chains are not proteolytically degraded (data not shown). Prior to thrombin kinetic analysis, the recombinant fibrinogens were dialyzed to remove the protease inhibitors.

EXAMPLE 8

Time Course of Thrombin-Catalyzed Fibrinopeptide Release

All kinetic reactions were in 50 mM Tris-HCl, pH=7.4, 0.15M NaCl, with the fibrinogen concentration of 0.4 $\mu$M, or approximately $0.1K_{mA}$, to simplify the kinetic analysis. The thrombin concentration was 0.043 U/ml for the reactions with B$\beta$ P70S-fibrinogen, and B$\beta$ L72S-fibrinogen; it was 0.43 U/ml for the reactions with B$\beta$ A68T-fibrinogen. The thrombin-catalyzed release of fibrinopeptides was measured by HPLC as described in Example 5. The quantity of fibrinopeptide was measured as the peak area, and the data were plotted as the % fibrinopeptide release where 100% is the maximum value for FpA release, as described in Example 6. Representative progress curves for each of the four recombinant fibrinogens are presented in FIG. 2.

The data for the time-dependent release of FpA were fitted, as previously described (Ng et al., Methods Enzymol. 222, 341 (1993)), to the first-order rate equation $$\% \text{FpA} = (1 - e^{k_1 t}) \times 100 \tag{1}$$

The data for the time-dependent release of FpB were fitted, as previously described (Ng et al., Methods Enzymol. 222, 341 (1993)) to the standard equation for two successive first order reactions; that is, the release of FpB is first order and follows the release of FpA:

$$\% \text{FpB} = (1 + [k_2/(k_1-k_2)]e^{-k_1 t} - [k_1/(k_1-k_2)]e^{-k_2 t}) \times 100 \tag{2}$$

In these equations, $k_1$ is the first-order rate constant for the release of FpA and $k_2$ is the first-order constant for the release of FpB. To determine $k_2$ for FpB release, we inserted the value of $k_1$ determined from the fit of FpA and we assumed that the maximal release of FpB was equal to that determined from the data for FpA.

The values for $k_1$ and $k_2$ are presented in Table 1. We found that only Bβ A68T-fibrinogen was a poor substrate for thrombin, so we increased the concentration of thrombin 10-fold for the reactions with this variant fibrinogen. The time course experiments were usually run in pairs, using a common diluted thrombin sample. As this dilution appeared to be a major variant in the experimental protocol, experiments using the same diluted thrombin sample are noted by superscript numerals. Because the substrate concentration is less than $0.1 K_m$ for FpA, and the $K_m$ for FpB is approximately the same as the $K_m$ for FpA (Martinelli & Scheraga, Biochemistry 19, 2343 (1980)), we determined the values for the specificity constant, $k_{cat}/K_m$, by dividing the kinetic constants by the concentration of thrombin. These data are presented in Table 2. Analysis of the specificity constants clearly demonstrated that fibrinopeptide release for Bβ A68T-fibrinogen was markedly impaired; the release of FpA from Bβ A68T-fibrinogen was 27-fold slower that from normal recombinant fibrinogen, and the release of FpB from Bβ A68T-fibrinogen was 45-fold slower that from normal fibrinogen. Analysis of the specificity constants also showed that FpA release from Bβ P70S-fibrinogen or Bβ L72S-fibrinogen was about 0.6 times the rate of normal recombinant fibrinogen but was not different from the rate of FpA release from plasmid fibrinogen. For FpB release, plasma fibrinogen and normal recombinant fibrinogen were essentially the same, while Bβ L72S-fibrinogen is about 0.8×and Bβ P70S-fibrinogen is about 0.6×that of normal recombinant fibrinogen. Thus, the rates of thrombin catalyzed fibrinopeptide release from these two variants were not substantially different from those of normal fibrinogen, whether plasma fibrinogen or normal recombinant fibrinogen. We note that these experiments indicated that FpA release from normal recombinant fibrinogen is about twice that of plasma fibrinogen. Subsequent experiments show that this difference is not reproducible. Gorkun et al., Blood 86 (Suppl. 1), Abstr. No. 3477 (1995).

TABLE 1

First-Order Rate Constants for Fibrinopeptide Release[a]

|  | plasma fib. | recombinant | Bβ A68T[b] | Bβ P70S | Bβ L72S |
| --- | --- | --- | --- | --- | --- |
| expt 1 |  |  |  |  |  |
| FpA | 0.19 ± 0.02[1c] | 0.23 ± 0.04 | 0.084 ± 0.005[3] | 0.11 ± 0.02[2] | 0.16 ± 0.03[1] |
| FpB | 0.062 ± 0.002 | 0.035 ± 0.001 | 0.012 ± 0.001 | 0.043 ± 0.005 | 0.037 ± 0.002 |
| expt 2 |  |  |  |  |  |
| FpA | 0.12 ± 0.03[2] | 0.21 ± 0.02[4] | 0.071 ± 0.005[4] | 0.11 ± 0.02[5] | 0.12 ± 0.01[5] |
| FpB | 0.064 ± 0.008 | 0.077 ± 0.009 | 0.013 ± 0.001 | 0.038 ± 0.001 | 0.062 ± 0.002 |
| expt 3 |  |  |  |  |  |
| FpA | 0.082 ± 0.03[6] | 0.19 ± 0.02[4] | 0.077 ± 0.005[4] | 0.14 ± 0.02[3] | 0.094 ± 0.011[6] |
| FpB | 0.093 ± 0.007 | 0.098 ± 0.011 | 0.016 ± 0.001 | 0.041 ± 0.002 | 0.068 ± 0.011 |
| av |  |  |  |  |  |
| FpA | 0.13 ± 0.02 | 0.21 ± 0.02 | 0.077 ± 0.004 | 0.12 ± 0.01 | 0.12 ± 0.01 |
| FpB | 0.067 ± 0.002 | 0.063 ± 0.004 | 0.014 ± 0.001 | 0.038 ± 0.002 | 0.051 ± 0.002 |

[a]Values are $k_1$ from eq 1 for FpA and $k_2$ from eq for FpB. Data are in min$^{-1}$.
[b]Data from Bβ A68T-fibrinogen were obtained with 0.43 units of thrombin/ml, while all other reactions were with 0.043 units of thrombin/ml.
[c]Superscript numerals (1–6) indicate experiments performed concurrently.

TABLE 2

Specificity Constants, $k_{cat}/K_m$, for FpA and FpB Release[a]

| substrate | FpA | FpB |
| --- | --- | --- |
| plasma fibrinogen | 5.4 | 2.8 |
| recombinant fibrinogen | 8.8 | 2.6 |
| Bβ A68T-fibrinogen | 0.32 | 0.058 |
| Bβ P70S-fibrinogen | 5.0 | 1.6 |
| Bβ L72S-fibrinogen | 5.0 | 2.1 |

[a]Values are x$10^6$ M$^{-1}$ s$^{-1}$.

EXAMPLE 9

Purification of Recombinant Fibrinogen by Immunoaffinity Chromatography

We also purified recombinant human fibrinogen by immunoaffinity chromatography using the IF-1 monoclonal antibody. The recombinant human fibrinogen was expressed in CHO cells as described in Example 3, and collected and concentrated with ammonium sulfate as described in Example 4, with three modifications. First, the pH of the medium was adjusted to 5.6 with 2-(N-morpholino)

ethanesulfonic acid (MES) buffer, pH 5.6, (final concentration, 20 mM MES) before fibrinogen was precipitated with ammonium sulfate. Second, 10 U/ml soybean trypsin inhibitor replaced aprotinin in all buffers. Third, immunoaffinity chromatography with the IF-1 monoclonal antibody replaced the protamine-SEPHAROSE® chromatography step described in Example 4.

Human plasma fibrinogen was also purified by IF-1 affinity chromatography as described above for recombinant human fibrinogen. Lyophilized plasma fibrinogen was dissolved in 50 mM Tris-HCl, pH 8.0, 0.3M NaCl, and dialyzed at 4° C. against 20 mM HEPES, pH 7.4, 0.15M NaCl. The fibrinogen solution was centrifuged at 13,000 g for 15 min (at 4° C.), and the supernatant was stored in aliquots at −70° C. prior to purification by immunoaffinity chromatography.

Fibrinogen was purified on an IF-1 conjugated SEPHAROSE 4B® column essentially as described previously. Takebe et al., Thromb. and Haemost. 73, 662 (1995). Monoclonal antibody IF-1 (10 mg) was coupled to 6 ml CNBr activated SEPHAROSE 4B®. An aliquot of plasma or recombinant fibrinogen was thawed, diluted to 0.5 mg/ml in 20 mM Tris-HCl, pH 7.4, 0.3M NaCl, 1 mM $CaCl_2$, 5 mM ε-ACA, 1 µM pepstatin, 1 µM leupeptin, 100 µM PMSF, 5 mM benzamidine, and 10 U/ml soybean trypsin inhibitor. The fibrinogen solution (15 ml) was loaded onto the IF-1 SEPHAROSE® column (1.6×3 cm) equilibrated with 20 mM Tris-HCl, pH 7.4, 0.3M NaCl, 1 mM $CaCl_2$. The column was washed sequentially with 20 mM Tris-HCl, pH 7.4, 0.3M NaCl, 1 mM $CaCl_2$ and 50 mM sodium acetate, pH 6.0, 0.3M NaCl, 1 mM $CaCl_2$, 50 ml each. Fibrinogen was eluted with 20 mM Tris-HCl, pH 7.4, 0.3 NaCl, 5 mM EDTA, and dialyzed against 20 mM HEPES, pH 7.4, 0.15M NaCl, 1 mM $CaCl_2$ at 4° C. The dialyzed sample was centrifuged at 13000 g for 15 min (at 4° C.) and the supernatant was stored in aliquots at −70° C.

EXAMPLE 10

SDS-PAGE and Western Blot Analysis

Reduced samples of fibrinogen were run on 10% gels, and non-reduced samples were run on 6% gels, both according to Laemmli. Laemmli, Nature 227, 680 (1970). Gels were stained with Coomassie Blue R-250, periodic acid-schiff stain for carbohydrate (Doerner & White, Analyt. Biochem. 187, 147 (1990)), or were electroblotted onto 0.45 µm nitrocellulose (BioRad). The blots were developed as described (Binnie et al., Biochemistry 32, 107 (1993)) with either a rabbit polyclonal antiserum (Dako) to fibrinogen, and alkaline phosphatase conjugated goat anti-rabbit antiserum (Pierce) or with monoclonal antibodies specific for individual chains—Y18 (Koppert et al., Blood 66, 503 (1985)) for the Aα chain, anti β (Valenzuela et al., Amer. J. Pathol. 141, 861 (1992)) for the Bβ chain and 4A5 (Shiba et al., Amer. J. Physiol. 260, C965 (1991)) for the γ chain—and alkaline phosphatase conjugated goat anti-mouse antiserum.

EXAMPLE 11

Characterization of Recombinant Human Fibrinogen

In order to accurately compare recombinant fibrinogen to plasma fibrinogen, we further purified commercial plasma fibrinogen by immunoaffinity chromatography as described in Example 9. SDS-PAGE analysis (data not shown) demonstrated that purified plasma fibrinogen was very similar to purified recombinant fibrinogen. Under non-reducing conditions, both samples appear as two high molecular weight bands, comparable to the previously described HMW and LMW fibrinogens (Holm et al., Thromb. Res., 37, 165 (1985)). It has been shown (Holm et al., Thromb. Res., 37, 165 (1985)) that these two proteins are complete, intact fibrinogen (HMW) and fibrinogen lacking a C-terminal fragment from the Aα chain (LMW). Under reducing conditions, both fibrinogen samples appear as three predominant bands that correspond to the Aα, Bβ, and γ chains of fibrinogen. Both samples also show a minor band, which, as described below, is a smaller Aα chain species, although the recombinant protein has less of this higher mobility species. When gels run under reducing conditions were stained for carbohydrate (data not shown), both fibrinogen samples appeared as two bands that align with the Bβ and γ chains. Thus, the chains in recombinant fibrinogen that were modified with carbohydrate have the same molecular weight as those known to be modified in plasma fibrinogen. We also examined fibrin monomers prepared from plasma and recombinant fibrinogens and found that the fibrin samples show comparable changes indicative of fibrinopeptide loss (data not shown).

We confirmed the identity of these bands by Western blot analysis (data not shown). Using a polyclonal antiserum that reacts with all three chains, we confirmed the similarity of recombinant fibrinogen to plasma fibrinogen. Blots developed with a monoclonal antibody that is specific for the Aα chain showed the heterogeneity of this chain in both plasma and recombinant fibrinogens (data not shown). Three Aα chain bands were seen for each sample, but the proportion of each band differed. Recombinant fibrinogen had a dominant band at 67 kDa, a secondary band at 55 kDa, and a faint band at 64 kDa. Plasma fibrinogen had a dominant band at 67 kDa, a secondary band at 64 kDa, and a faint band at 55 kDa. Blots developed with monoclonal antibodies specific for the Bβ and γ chains demonstrated the similar size and homogeneity of these chains in the recombinant and plasma fibrinogens (data not shown).

EXAMPLE 12

Figure 3:
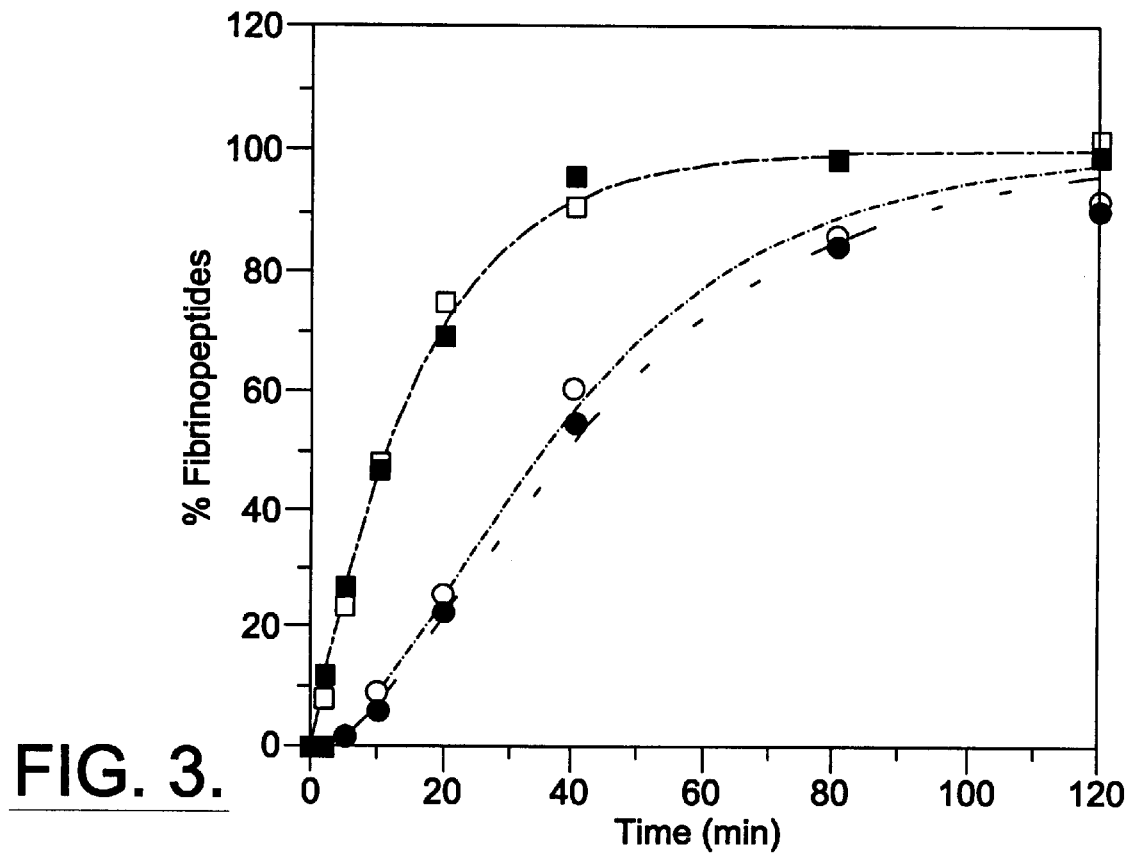
FIG. 3 presents the progress curves for fibrinopeptide release from immunoaffinity purified fibrinogen. Thrombin-catalyzed release of fibrinopeptides from plasma fibrinogen, dashed lines, FpA (□) and FpB (○); and recombinant fibrinogen, dotted line, FpA (■) and FpB (●), was monitored by HPLC. The data were fitted to first-order rate equations, assuming FpA is released prior to FpB, as described in Example 8 and the legend to FIG. 2.

Thrombin-catalyzed Release of Fibrinopeptides From Immunoaffinity Purified Recombinant Fibrinogen and Plasma Fibrinogen The thrombin-catalyzed release of FpA and FpB was followed by HPLC as described in Example 5. The samples contained 0.1 mg/ml fibrinogen (0.3 µM) and 0.01 U/ml (0.1 nM) of human α-thrombin in 20 mM HEPES, pH 7.0, 0.15M NaCl, 5 mM ε-ACA and 1 mM $CaCl_2$. The reactions were performed at ambient temperature, and the released fibrinopeptides were separated by reversed-phase HPLC. The data were plotted as % fibrinopeptide release, and were fitted to progress curves assuming the reactions are first order, as described in Example 6. All experiments were performed three times. The average curves are shown in FIG. 3, and the kinetic analysis are summarized in Table 3. These data demonstrated that the rate of fibrinopeptide release from recombinant fibrinogen was essentially the same as from plasma fibrinogen.

TABLE 3

First-Order Rate Constants for Fibrinopeptide Release[a]

|  | Plasma fibrinogen | Recombinant fibrinogen |
|---|---|---|
| experiment 1 | | |
| FpA | 0.059 ± 0.007 | 0.055 ± 0.004 |
| FpB | 0.042 ± 0.001 | 0.040 ± 0.003 |
| experiment 2 | | |
| FpA | 0.065 ± 0.010 | 0.065 ± 0.003 |
| FpB | 0.037 ± 0.003 | 0.031 ± 0.002 |
| experiment 3 | | |
| FpA | 0.063 ± 0.007 | 0.072 ± 0.004 |
| FpB | 0.029 ± 0.003 | 0.029 ± 0.001 |
| average | | |
| FpA | 0.062 ± 0.008 | 0.064 ± 0.004 |
| FpB | 0.036 ± 0.002 | 0.033 ± 0.002 |

[a]Values of $k_1$ for FpA and $k_2$ for FpB were calculated as described in Example 8 and are in $min^{-1}$.

EXAMPLE 13

Fibrin Monomer Preparation

Fibrin monomer was prepared by clotting fibrinogen with thrombin as described previously (Belitser et al., Biochim. et Biophys Acta 154, 367 (1968)) with modifications. Fibrinogen was dialyzed against 20 mM HEPES, pH 7.4, 0.15M NaCl, 5 mM ε-ACA at 4° C. overnight, and diluted to 0.3 mg/ml in the same buffer. Thrombin was diluted to 1.1 U/ml in the same buffer immediately prior to the reaction. Thrombin (40 μl) was added to 400 μl of fibrinogen on ice, vortexed gently, and incubated at 37° C. In three hours the clot was wrapped around a glass rod made from a 50 μl glass capillary with sealed ends. The clot was washed in 5 ml of 0.15M NaCl solution, 10 times, 5 min for every change. This is a critical step that removes buffer from the clot, thereby making it easier to dissolve fibrin in 40 μl of ice-cold, 0.125% acetic acid. The dissolved fibrin monomer was re-polymerized by 10-fold dilution in 20 mM HEPES, pH 7.4, 0.15M NaCl, 5 mM ε-ACA, incubated at ambient temperature for three hours, and dissolved in ice-cold acetic acid. The repolymerization procedure was repeated twice. The resulting fibrin monomer solution was clarified by centrifugation (13000 g, 10 min, 4° C.) and left at 4° C. for two days, to allow the fibrin polymers to completely dissociate. The fibrin monomer preparation was stored at 4° C. and used within one month.

EXAMPLE 14

Polymerization Turbidity Curves

Polymerization of fibrinogen or fibrin monomer was measured by turbidity changes with time at 350 nm using a Shimadzu UV-260 spectrophotometer equipped with a thermostatic cuvette holder. Fibrinogen (90 μl of 0.1 mg/ml), dialyzed against 20 mM HEPES, pH 7.4, 0.15M NaCl, 5 mM ε-ACA, 0.1 mM $CaCl_2$ was placed in a 100 μl microcuvette with a 10 mm optical path (Starna Cells, Inc.). Thrombin (10 μl of 1 U/ml) was added at zero time, and the change of turbidity with time was recorded. Fibrin monomer (10 μl of 2 mg/ml, in 0.125% acetic acid) was added to 90 μl of 20 mM HEPES, pH 7.4, 0.15M NaCl, 5 mM ε-ACA at zero time, and the change of turbidity was recorded. All polymerization experiments were performed at 25° C.

EXAMPLE 15

Polymerization of Fibrin Monomers

Figure 4:
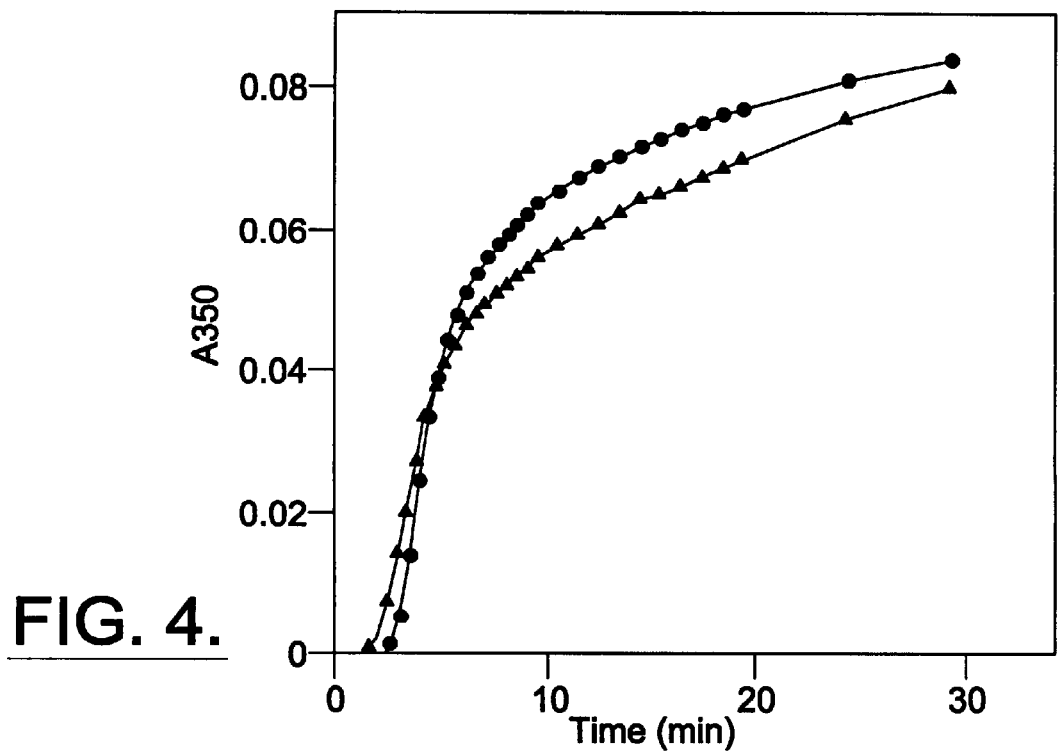
FIG. 4 shows thrombin-catalyzed polymerization of plasma and recombinant fibrinogens. Polymerization was initiated by the addition of thrombin at time 0 (0.1 U/ml) to recombinant (●) or plasma (▲) fibrinogen (0.9 mg/ml) and polymer formation was measured as change in turbidity at 350 nm with time.

Polymerization of fibrin monomers prepared as described in Example 13 was measured as the change in turbidity at 350 nm, as described in Example 14. The reactions were performed at 25° C., using the same sample conditions as the fibrinopeptide release reaction described in Example 5, except for a reduction in $CaCl_2$ to 0.1 mM. Representative curves are shown in FIG. 4. We characterized the curves by two quantitative measures—the lag period, which represents the time required for protofibril formation, and the maximum slope, which reflects the rate of assembly of protofibrils. The data are presented in Table 4. This analysis demonstrated that, on average, the lag period was about 1.2-fold longer and the maximum slope was about 1.6-fold steeper for recombinant fibrinogen relative to plasma fibrinogen.

Figure 5:
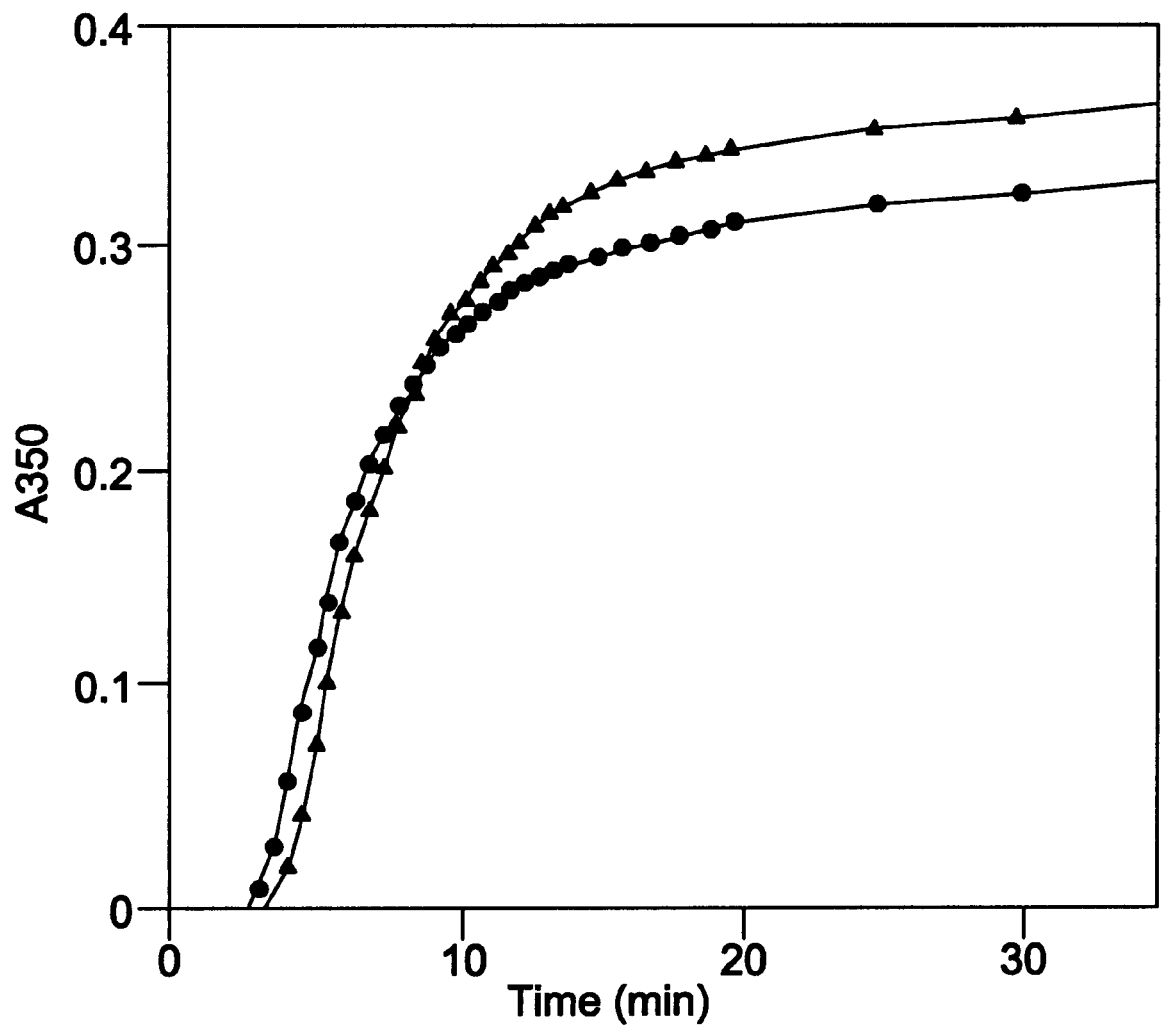
FIG. 5 shows polymerization of plasma and recombinant fibrin monomers. Fibrin monomers (2 mg/ml) prepared from plasma fibrinogen (●) and recombinant fibrinogen (▲) were diluted 10-fold into neutral buffer at time 0, and the change in turbidity monitored at 350 nm with time.

In order to circumvent the contribution of thrombin catalysis to polymerization (Weisel et al., J. Mol. Biol. 232, 285 (1993)), we examined polymerization of fibrin monomers prepared from each of these fibrinogens, as described in Example 13. Polymerization was initiated by diluting fibrin monomers dissolved in 0.125% acetic acid with buffer at neutral pH, and the changes in turbidity were monitored as for the thrombin-catalyzed reactions. Representative curves are shown in FIG. 5, and the quantitative data are presented in Table 4. On average, we found that the lag period with recombinant fibrin monomer was 1.2-fold longer than with plasma fibrin monomer, and we found no difference between the maximum slopes observed with recombinant monomer and plasma monomer.

TABLE 4

Polymerization Parameters

| | Protein concentration | Experiment number | Lag-period (sec) | Maximum Rate ($x10^{-5}$ $sec^{-1}$) |
|---|---|---|---|---|
| Plasma fibrinogen | 0.1 mg/ml | 1 | 135 | 25 |
| | 0.1 mg/ml | 2 | 144 | 22 |
| | 0.1 mg/ml | 3 | 138 | 21 |
| | | avg. | 139 ± 4 | 23 ± 2 |
| Recombinant fibrinogen | 0.1 mg/ml | 1 | 150 | 41 |
| | 0.1 mg/ml | 2 | 190 | 40 |
| | 0.1 mg/ml | 3 | 166 | 29 |
| | | avg. | 169 ± 16 | 37 ± 5 |
| Plasma fibrin monomer | 0.2 mg/ml | 1 | 180 | 118 |
| | 0.2 mg/ml | 2 | 210 | 108 |
| | 0.2 mg/ml | 3 | 183 | 108 |
| | | avg. | 191 ± 13 | 111 ± 5 |
| Recombinant fibrin monomer | 0.2 mg/ml | 1 | 219 | 110 |
| | 0.2 mg/ml | 2 | 234 | 97 |
| | 0.2 mg/ml | 3 | 250 | 120 |
| | | avg. | 234 ± 13 | 109 ± 10 |

EXAMPLE 16

FXIIIa Catalyzed Cross-linking of Fibrin

Polymerization of fibrinogen (0.38 mg/ml) in the absence or presence of Factor XIIIa (FXIIIa) (0.5 μg/ml; 1.1 U/ml final concentration) was initiated with addition of human α-thrombin (1 U/ml final concentration). The reactions were run at room temperature in 20 mM HEPES, pH 7.4, 150 mM NaCl, 5 mM ε-ACA, 1 mM CaCl$_2$, and terminated at selected intervals by addition of SDS and 2-mercaptoethanol to 1% and 2% final concentration, respectively. The samples were analyzed by SDS-PAGE on 10% gels. Controls labeled 0 min were prepared by adding SDS and 2-mercaptoethanol to fibrinogen before thrombin and FXIIIa.

We followed FXIIIa catalyzed cross-link formation by SDS-PAGE under reducing conditions. Previous work has demonstrated that γ chain dimers are the first products of FXIII transglutaminase activity. Lorand, Ann. N.Y. Acad. Sci. 202, 6 (1972). γ chain dimers were evident after 2 minutes in reactions with either plasma or recombinant fibrinogen (data not shown). Furthermore, the accumulation of γ chain dimers and the loss of γ chain monomers followed similar patterns for these two proteins. Very small amounts of γ chain dimers were also seen in the absence of added FXIIa, as expected if the plasma fibrinogen was contaminated with plasma FXIII; these bands were not found with recombinant fibrinogen in the absence of added FXIIIa (data not shown). We also noted that the products with plasma fibrinogen appeared as a pair; the higher molecular weight product may contain the larger γ' chain, which is present in plasma fibrinogen but not in recombinant fibrinogen. The differences between the results obtained with plasma and recombinant fibrinogen are thus consistent with known characteristics of plasma fibrinogen, the presence of the γ' chain, and contamination with FXIII. We therefore concluded that the kinetics of cross-link formation and the nature of the cross-linked products were comparable for recombinant and plasma fibrinogens.

EXAMPLE 17

Transmission and Scanning Electron Microscopy

Rotary-shadowed samples were prepared by spraying a fibrinogen solution (30 μg/ml) in 0.05M ammonium formate, pH 7.4, and 25% glycerol onto freshly cleaved mica and shadowing with tungsten in a vacuum evaporator. Weisel et al., Science 230, 1388 (1985); Veklich et al., J. Biol. Chem. 268, 13577 (1993). Transmission electron microscopy was carried out on a Philips-400 electron microscope at 80 kV and magnification of 60000x.

Fibrin samples for scanning electron microscopy were prepared in 20 mM HEPES, pH 7.4, 0.15M NaCl, 5 mM ε-ACA in the following way: 180 μl of fibrinogen (0.55 mg/ml) was placed in small polyethylene tubes sealed on one end with PARAFILM®. Then 20 μl of thrombin (5 U/ml) was added and mixed quickly to start polymerization. Final concentration of fibrinogen was 0.5 mg/ml and thrombin was 0.5 NIH units/ml. After one hour at room temperature, 0.6 ml of 2% glutaraldehyde was placed on the top of the formed clot. This solution was replaced with a fresh one three times during one hour. After the clot was fixed, the PARAFILM® was carefully removed followed by rinsing, dehydration and critical-point drying. Langer et al., J. Biol. Chem. 263, 15056 (1988). Clots formed by fibrin monomers were prepared in the same way with polymerization initiated by 10-fold dilution of fibrin-monomer solution (5 mg/ml) into the 20 mM HEPES, pH 7.4, 0.15M NaCl, 5 mM ε-ACA. Photographs of all clots were recorded digitally with a Philips XL20 scanning electron microscope at 10 kV and analyzed using the NIH Image program. The data were analyzed using the software STATVIEW® from ABACUS and reported with the standard deviation.

EXAMPLE 18

Electron Microscopy of Fibrinogen and Fibrin Clots

Individual fibrinogen molecules were examined by electron microscopy of samples prepared by rotary shadowing as described in Example 17. Trinodular molecules similar to those reported previously (Erickson & Fowler, Ann. N.Y. Acad. Sci., 408, 146 (1983); Veklich et al., J. Biol. Chem. 268, 13577 (1993)) were seen in all preparations (data not shown). The appearance of more than 450 molecules was analyzed with particular attention focused toward additional nodules either near the central domain or near the lateral domains. Quantitative data are presented in Table 5. Clearly, the overall shape of the molecules of the recombinant fibrinogen was essentially the same as that of the plasma fibrinogen. The fraction of molecules containing a fourth nodule was reduced with recombinant fibrinogen. Because the fourth nodule is thought to be the C-terminal domain of the Aα chain (Erickson & Fowler, Ann. N.Y. Acad. Sci., 408, 146 (1983); Veklich et al., J. Biol. Chem. 268, 13577 (1993)), this result indicated a potential difference in the Aα chain structures of plasma and recombinant fibrinogen.

We also examined clot structure by scanning electron microscopy. Clottability of the purified fibrinogens was determined as previously described (Birken et al., Thromb. Res. 7, 599 (1975)), using human α-thrombin and 20 mM HEPES, pH 7.4, 0.15M NaCl, 5 mM ε-ACA, 1 mM CaCl$_2$. Clottability was 98% for plasma fibrinogen and 96% for recombinant fibrinogen.

The appearance of clots prepared from recombinant and plasma fibrinogens, and their respective fibrin monomers, were very similar (data not shown). Clots prepared from plasma fibrinogen and recombinant fibrinogen both showed extensively branched fiber networks. As has been previously seen (Weisel et al., J. Mol. Biol. 232, 285 (1993)), the degree of lateral aggregation and the pore size were significantly greater for clots prepared from fibrin monomers versus those prepared by thrombin activation of fibrinogen (data not shown). This was true for both recombinant and plasma fibrinogens. The diameters of several hundred fibers were measured from micrographs of clots formed from plasma fibrinogen and recombinant fibrinogen. The mean diameter for plasma fibrinogen fibers was 91±15 nm and the mean diameter for recombinant fibrinogen fibers was 84±13 nm. For clots prepared from fibrin monomers of plasma fibrinogen and recombinant fibrinogen, the mean diameters were 138±25 nm and 132±23 nm, respectively. Thus, there were no obvious differences when comparing clots formed from recombinant to plasma fibrinogen.

TABLE 5

Shapes of Individual Molecules Observed for Plasma and Recombinant Fibrinogen

| Sample | No. molecules examined | Percentage of molecules with the appearance | | |
|---|---|---|---|---|
| Plasma fibrinogen | 559 | 63 | 22 | 15 |
| Recombinant fibrinogen | 457 | 77 | 15 | 8 |

That which is claimed is:

1. A method for the production of recombinant fibrinogen, comprising the steps of:
   growing mammalian cells that express recombinant fibrinogen in a serum-free medium under conditions that cause the expression of fibrinogen in the medium at a level of greater than 1 μg/ml; then
   collecting at least a portion of the medium containing greater than 1 μg/ml of recombinant fibrinogen, wherein said growing step is carried out for three or more weeks prior to said collecting step; and then
   concentrating the fibrinogen from the medium to form a concentrated medium, wherein the fibrinogen is concentrated in the presence of at least one protease inhibitor; and then
   purifying the fibrinogen from the medium by affinity chromatography.

2. A method according to claim 1, wherein the purifying step is carried out by affinity chromatography with a polyclonal antibody.

3. A method according to claim 1, wherein said purifying step is carried out by affinity chromatography with a monoclonal antibody.

4. A method according to claim 1, wherein said purifying step is carried out by affinity chromatography with a peptide having high affinity for fibrinogen.

5. A method according to claim 1, wherein said purifying step is carried out by affinity chromatography with protamine-agarose.

6. A method according to claim 1, wherein said concentrating and purifying steps are carried out in the presence of at least one protease inhibitor.

7. A method according to claim 1, wherein said concentrating and purifying steps are carried out in the presence of at least two protease inhibitors.

8. A method according to claim 1, wherein the at least one protease inhibitor is selected from the group consisting of soybean trypsin inhibitor, aprotinin, pepstatin, benzamide, benzamidine, sodium p-hydroxymercuribenzoate, iodoacetate, N-ethylmaleimide, diazoacetyinorleucine methyl ester, leupeptin, ε-aminocaproic acid, antipain, ethylenediaminetetraacetic acid, ethylene glycol bis(β-aminoethyl ether) N,N,N',N'-tetraacetic acid, and phenylmethylsufonyl fluoride.

9. A method according to claim 1, wherein said growing step is carried out for a time of two to three months.

10. A method according to claim 1, wherein the fibrinogen is expressed in the medium at a level of greater than 10 μg/ml.

11. A method according to claim 1, wherein said concentrating step is carried out by precipitation with a 20–55% saturated solution of ammonium sulfate.

12. A method according to claim 1, wherein the recombinant fibrinogen is a mutant fibrinogen.

13. A method for the production of recombinant fibrinogen, comprising the steps of:

growing mammalian cells that express recombinant fibrinogen in a serum-free medium under conditions that cause the expression of fibrinogen in the medium at a level greater than 10 μg/ml; then collecting at least a portion of the medium containing greater than 10 μg/ml of recombinant fibrinogen; and then concentrating the fibrinogen from the medium to form a concentrated medium, wherein the fibrinogen is concentrated in the presence of at least one protease inhibitor; and then purifying the fibrinogen from the medium by affinity chromatography with protamine-agarose.

14. A method according to claim 13, wherein said concentrating and purifying steps are carried out in the presence of at least one protease inhibitor.

15. A method according to claim 13, wherein said concentrating and purifying steps are carried out in the presence of at least two protease inhibitors.

16. A method according to claim 13, wherein the at least one protease inhibitor is selected from the group consisting of soybean trypsin inhibitor, aprotinin, pepstatin, benzamide, benzamidine, sodium p-hydroxymercuribenzoate, iodoacetate, N-ethylmaleimide, diazoacetyinorleucine methyl ester, leupeptin, ε-aminocaproic acid, antipain, ethylenediaminetetraacetic acid, ethylene glycol bis(β-aminoethyl ether) N,N,N',N'-tetraacetic acid, and phenylmethylsufonyl fluoride.

17. A method according to claim 13, wherein said concentrating step is carried out by precipitation with a 20–55% saturated solution of ammonium sulfate.

18. A method according to claim 13, wherein said concentrating step is carried out by precipitation with a 40% or greater saturated solution of ammonium sulfate.

19. A method according to claim 13, wherein the recombinant fibrinogen is a mutant fibrinogen.

20. A method for the production of recombinant fibrinogen, comprising the steps of:

growing mammalian cells that express recombinant fibrinogen in a serum-free medium under conditions that cause the expression of fibrinogen in the medium at a level of at least 1 μg/ml; then collecting at least a portion of the medium containing at least 1 μg/ml of recombinant fibrinogen, wherein said growing step is carried out for three or more weeks prior to said collecting step; and then concentrating the fibrinogen from the medium to form a concentrated medium, wherein the fibrinogen is concentrated in the presence of at least one protease inhibitor; and then purifying the fibrinogen from the medium by immunoprecipitation.

21. A method according to claim 20, wherein said purifying step is carried out by immunoprecipitation with a polyclonal antibody.

22. A method according to claim 20, wherein said purifying step is carried out by immunoprecipitation with a monoclonal antibody.

23. A method according to claim 20, wherein said purifying step is carried out by immunoprecipitation with a 40% or greater saturated solution of ammonium sulfate.

24. A method for the production of recombinant fibrinogen, comprising the steps of:

growing mammalian cells that express recombinant fibrinogen in a serum-free medium under conditions that cause the expression of fibrinogen in the medium at a level greater than 10 μg/ml; then collecting at least a portion of the medium containing greater than 10 μg/ml of recombinant fibrinogen; and then concentrating the fibrinogen from the medium to form a concentrated medium, wherein said concentrating step is carried out in the presence of at least one protease inhibitor; and then purifying the fibrinogen from the medium by affinity chromatography with a monoclonal antibody.

25. A method according to claim 24, wherein said concentrating and purifying steps are carried out in the presence of at least one protease inhibitor.

26. A method according to claim 24, wherein said concentrating and purifying steps are carried out in the presence of at least two protease inhibitors.

27. A method according to claim 24, wherein the at least one protease inhibitor is selected from the group consisting of soybean trypsin inhibitor, aprotinin, pepstatin, benzamide, benzamidine, sodium p-hydroxymercuribenzoate, iodoacetate, N-ethylmaleimide, diazoacetylnorleucine methyl ester, leupeptin, ε-aminocaproic acid, antipain, ethylenediaminetetraacetic acid, ethylene glycol bis(β-aminoethyl ether) N,N,N',N'-tetraacetic acid, and phenylmethylsufonyl fluoride.

28. A method according to claim 24, wherein said growing step is carried out for three or more weeks prior to said collecting step.

29. A method according to claim 24, wherein said concentrating step is carried out by precipitation with a 20–55% saturated solution of ammonium sulfate.

30. A method according to claim 24, wherein said concentrating step is carried out by precipitation with a 40% or greater saturated solution of ammonium sulfate.

31. A method according to claim 24, wherein the recombinant fibrinogen is a mutant fibrinogen.

32. A method for the production of recombinant fibrinogen, comprising the steps of:

growing mammalian cells that express recombinant fibrinogen in a serum-free medium under conditions that cause the expression of fibrinogen in the medium at a level of at least 1 μg/ml; then collecting at least a portion of the medium containing greater than 1 μg/ml of recombinant fibrinogen, wherein said growing step is carried out for three or more weeks prior to said collecting step; and then concentrating the fibrinogen from the medium to form a concentrated medium, wherein said concentrating step is carried out in the presence of at least one protease inhibitor; and then purifying the fibrinogen from the medium by anion-exchange chromatography.

33. A method according to claim 32, wherein said concentrating and purifying steps are carried out in the presence of at least one protease inhibitor.

34. A method according to claim 32, wherein said concentrating and purifying steps are carried out in the presence of at least two protease inhibitors.

35. A method according to claim 32, wherein said growing step is carried out for a time of two to three months.

36. A method according to claim 32, wherein said concentrating step is carried out by precipitation with a 20–55% saturated solution of ammonium sulfate.

37. A method according to claim 32, wherein said concentrating step is carried out by precipitation with a 40% or greater saturated solution of ammonium sulfate.

38. A method according to claim 32, wherein the recombinant fibrinogen is a mutant fibrinogen.

39. A method for the production of recombinant fibrinogen, comprising the steps of:

growing mammalian cells that express recombinant fibrinogen in a serum-free medium under conditions that cause the expression of fibrinogen in the medium at a level greater than 10 μg/ml; then collecting at least a portion of the medium containing greater than 10 μg/ml of recombinant fibrinogen; and then concentrating the fibrinogen from the medium to form a concentrated medium, wherein said concentrating step is carried out in the presence of at least one protease inhibitor; and then purifying the fibrinogen from the medium by anion-exchange chromatography.

40. A method according to claim 39, wherein said concentrating and purifying steps are carried out in the presence of at least one protease inhibitor.

41. A method according to claim 39, wherein said concentrating and purifying steps are carried out in the presence of at least two protease inhibitors.

42. A method according to claim 39, wherein said growing step is carried out for three or more weeks prior to said collecting step.

43. A method according to claim 39, wherein said concentrating step is carried out by precipitation with a 20–55% saturated solution of ammonium sulfate.

44. A method according to claim 39, wherein the recombinant fibrinogen is a mutant fibrinogen.

* * * * *